(12) United States Patent
Hayashida et al.

(10) Patent No.: US 6,576,320 B2
(45) Date of Patent: Jun. 10, 2003

(54) OPTICAL INFORMATION MEDIUM AND EVALUATION METHOD

(75) Inventors: Naoki Hayashida, Chuo-ku (JP); Hideki Hirata, Chuo-ku (JP); Toshifumi Tanaka, Chuo-ku (JP)

(73) Assignee: TDK Corporation, Tokyo (JP)

( * ) Notice: Subject to any disclaimer, the term of this patent is extended or adjusted under 35 U.S.C. 154(b) by 0 days.

(21) Appl. No.: 09/891,250

(22) Filed: Jun. 27, 2001

(65) Prior Publication Data

US 2002/0054975 A1 May 9, 2002

(30) Foreign Application Priority Data

Jun. 28, 2000 (JP) .................... 2000-195045
Dec. 28, 2000 (JP) .................... 2000-402926
Jun. 11, 2001 (JP) .................... 2001-176374

(51) Int. Cl.$^7$ ................................ B32B 3/02
(52) U.S. Cl. ............. 428/64.1; 428/64.4; 430/270.11
(58) Field of Search ................... 428/64.1, 64.4, 428/457, 447, 913; 430/270.11, 475.1, 945

(56) References Cited

U.S. PATENT DOCUMENTS 5,846,649 A * 12/1998 Knapp .................... 428/334

FOREIGN PATENT DOCUMENTS

| JP | 6-187663 | * | 7/1994 |
| JP | 8-263878 | * | 10/1996 |
| JP | 11-203726 | * | 7/1999 |
| JP | 11-213444 | * | 8/1999 |
| JP | 2000-132865 | * | 5/2000 |

* cited by examiner

Primary Examiner—Elizabeth Mulvaney
(74) Attorney, Agent, or Firm—Oblon, Spivak, McClelland, Maier & Neustadt, P.C.

(57) ABSTRACT

An optical information medium has a light-transparent substrate and an information recording layer, wherein optical recording and/or reading is performed with a laser beam that enters the information recording layer from the light-transparent substrate side. A cured polysilazane film is disposed on the laser beam incident side of the light-transparent substrate, and the light-transparent substrate or the light-transparent substrate having the cured polysilazane film integrated thereon has a tensile modulus of at least 200 MPa. The medium on its laser beam incident side surface is improved in mar resistance.

11 Claims, 6 Drawing Sheets

LASER BEAM

LASER BEAM

OPTICAL INFORMATION MEDIUM AND EVALUATION METHOD

BACKGROUND OF THE INVENTION

1. Technical Field

This invention relates to optical information media such as read-only optical disks and optical recording disks, and a method for evaluating the mar resistance of the same.

2. Background Art

To accommodate a vast quantity of information as typified by moving image data, advanced optical information media are required to increase their recording density. Active research and development works have been made to achieve a higher density for increasing the recording capacity. Among such research works, one proposal relating to digital versatile disks (DVD) is to shorten the wavelength of recording/reading light and increase the numerical aperture (NA) of an objective lens, thereby reducing the focused spot diameter of recording/reading light. As compared with compact disks (CD), DVD is successful in achieving a recording capacity of 6 to 8 folds (typically 4.7 GB/side) by changing the recording/reading wavelength $\lambda$ from 780 nm to 650 nm and the numerical aperture from 0.45 to 0.60.

For long-term recording of moving images of quality, an attempt was recently made to achieve a recording capacity of at least 4 folds of that of DVD by reducing the recording/reading wavelength to about 400 nm and increasing the numerical aperture to about 0.85.

However, several problems arise in establishing such a recording/reading system having increased NA. One exemplary problem is a reduction of the tolerance for the tilt of the information recording layer of the medium. More particularly, as is well known in the art, the tilt margin, that is a permissible tilt of the information recording layer relative to incident light, is in proportion to $\lambda/[t\times(NA)^3]$ wherein $\lambda$ denotes the wavelength of recording/reading light and "t" denotes the thickness of a substrate. The tilt margin dramatically declines as the NA increases.

Also if the optical recording medium is inclined or tilted, a wavefront aberration (or coma) occurs. The coefficient of wavefront aberration W is represented by the formula I below.

$$W = (½) \times t \times \{n^2 \times \sin\theta \times \cos\theta\} \times NA^3 / (n^2 - \sin^2\theta)^{-5/2} \quad \text{Formula I}$$

In formula I, n denotes the refractive index of the transparent substrate (referred herein as light-transparent substrate) by which a recording/reading laser beam is transmitted before reaching the information recording layer and $\theta$ is a tilt angle. It is appreciated from formula I that the thickness of the light-transparent substrate must be reduced in order to acquire a certain tilt margin.

For this reason, the DVD is given a tilt margin by reducing the thickness of the light-transparent substrate to about one half (about 0.6 mm) of the thickness (about 1.2 mm) of the conventional CD substrate. For the system with a NA equal to 0.85, the thickness of the light-transparent substrate is reduced to about 0.1 mm.

Other problems associated with the increased NA are reduced focal depth and reduced working distance between the light-transparent substrate surface and the objective lens. The focal depth decreases in inverse proportion to $(NA)^2$ and so, the focusing servo system is likely to become unstable and consequently, very sensitive to mechanical precision, flaws and stains on the light-transparent substrate surface. Moreover, the working distance decreases as the NA increases, provided that the objective lens diameter is fixed, with the increased risk of collision of the pickup casing or objective lens against the light-transparent substrate surface. For example, the system with NA=0.85 will have a focal depth of ±0.3 μm and a working distance of about 100 to 300 μm so that the focusing servo system is likely to become very unstable.

Also, objective lenses are generally made of plastics and glass, and it is a common practice to provide a protective plate around the lens as a precaution to the possible contact of the lens with the light-transparent substrate surface. In the case of a plastic lens, a protective plate known as edge guard is integrally molded for the protection of the lens surface. In the case of a glass lens, a plate of plastic material such as acrylic resin or polypropylene is attached around the lens as a lens protector. The general design is such that even if the pickup contacts the disk, the protective plate portion comes in preferential contact to prevent the objective lens surface from being flawed.

Meanwhile, most optical disks now available in the market use rigid substrates of thermoplastic resins such as polycarbonate and polymethyl methacrylate as the light-transparent substrate. This means that data are recorded and reproduced with a laser beam which enters the information recording layer past the surface of these resinous substrates. These resins are optically homogeneous, highly transparent, easily moldable and excellent in mechanical strength, but have drawbacks including a low surface hardness and mar susceptibility. It is then a common practice to provide the resinous substrate on its surface with any hard coat layer as the mar-proof layer. In forming such hard coat layers, it is most customary to apply a polymerization curable compound having at least two polymerizable functional groups such as acryloyl groups in a molecule to the substrate surface, and irradiating thereto actinic radiation such as UV radiation for curing for thereby forming a hard coat layer.

However, these resins of the UV curing type have a certain limit of surface hardness achievable, despite superior abrasion resistance as compared with thermoplastic resins including polycarbonate, and do not always provide fully satisfactory abrasion resistance for use as optical information media. The system in which a high density is achieved by increasing the NA of the recording/reading optical system requires that disks be protected from not only damages during the user's handling of the disk, but also damages by the above-mentioned collision of the pickup. Accordingly, there is a need for a hard coat layer which has a dramatically improved hardness as compared with the aforementioned UV-curable resins.

To solve such a problem, methods for forming hard coat layers based on inorganic compounds have been proposed.

For example, JP-A 11-203726 discloses a method of forming a hard coat layer on an optical disk having a recording layer and a light-transparent layer successively stacked on a substrate, wherein recording and/or reading is performed with incident light from the light-transparent layer side, the method involving the steps of depositing inorganic materials such as SiN and SiO on the light-transparent layer surface as two or more layers by an ion beam sputtering or similar technique, the deposited layers serving as a protective film or hard coat layer. However, the inorganic film formed by such a technique as sputtering or evaporation has increased internal stresses. Then, when the film is grown to a thickness of more than several hundreds of nanometers in order to establish satisfactory abrasion resistance, the film becomes self-destructible. Then the inorganic film of this type is difficult to provide a hard coat layer having substantially satisfactory abrasion resistance.

JP-A 8-263878 proposes a method of forming a silica-based thin film on a substrate surface by a sol-gel process using a solution of alkoxysilane or the like, the thin film serving as a protective film or hard coat layer. When the inorganic compound film is formed by the sol-gel process, however, baking at a high temperature in extreme excess of 100° C. is necessary to promote the reaction to a full extent to form a consolidated film. It is then difficult to apply this method to the surface of light-transparent substrates made of less heat resistant resins.

JP-A 2000-132865 describes an information recording medium having a protective layer made of polysilazane. The subject matter of this patent publication is an information recording medium having a disk or tape-shaped support, although the publication lacks an example in which the invention is applied to optical disks.

While the surface hardness serves as an index of the abrasion resistance of resinous materials or inorganic materials used as the hard coat layer, it is generally measured as indentation hardness (as typified by Vickers hardness) or scratch hardness, or by an abrasion test. Of these measuring methods, in the abrasion test, for example, the abrasion loss of a test specimen resulting from abrasion is often quantitatively determined using changes of several parameters such as the weight, thickness and light transmittance of the test specimen. For optically transparent materials having a relatively high surface hardness like the hard coat layer materials for optical information media, it is most adequate to quantitatively determine the hardness using a change of light transmittance or light diffusion. Specifically, it is customary to measure the haze of the test specimen on which white parallel light is incident.

The method of evaluating the hardness of a specimen utilizing haze measurement is effective as a method of quantitatively determining the visual deterioration of a specimen caused by abrasion. However, this evaluation method offers macroscopic evaluation using incoherent light, that is, non-convergent light, which is not always correlated to the degree of deterioration of recording/reading characteristics of the optical information medium caused by abrasion. Therefore, the above method is not regarded as an appropriate method of evaluating the performance of a hard coat layer on an optical information medium. Additionally, the evaluation method based on haze measurement is to measure the light transmitted by a transparent specimen, and so, in evaluating a hard coat layer on an optical information medium, a self-supporting film equivalent to the hard coat layer must be previously furnished before measurement can be made. On the other hand, the abrasion resistance of the hard coat layer depends on the surface property, coefficient of friction, and thickness of the hard coat layer and the modulus of elasticity of the material of which the hard coat layer is made although the factors governing the abrasion resistance are not limited thereto. For example, the hardness of the substrate on which the hard coat layer is formed also has a substantial influence on the abrasion resistance of the hard coat layer at its surface. Accordingly, in this regard too, for accurate evaluation of the performance of a hard coat layer, it is preferred to evaluate the hard coat layer as actually formed on an optical information medium.

Heretofore, there has not been available a method of evaluating or inspecting a hard coat layer while meeting various requirements as mentioned above, and it has been impossible to ascertain the accurate performance of a hard coat layer. However, an optical disk system having a capacity increased due to the reduced wavelength and increased NA of a recording/reading optical system, which is now under investigation for practical use, is more sensitive to flaw and stain on the surface of a light-transparent substrate than the existing CDs and DVDs. Accordingly, the requirements on the abrasion resistance and mar resistance of the hard coat layer become more strict than in the prior art, and there is a strong desire to have a method suitable for the quantitative determination of these properties.

Also where the light-transparent substrate as a whole is constructed of a high hardness material rather than the provision of a hard coat layer on the surface of a light-transparent substrate, the mar resistance of the light-transparent substrate can be altered by such means as forming a recording layer or joining together with another substrate. Accordingly, in this case too, there is a desire to have a method capable of evaluating the mar resistance of a light-transparent substrate under the same conditions as in actual media.

SUMMARY OF THE INVENTION

The present invention has been devised under the above-mentioned circumstances, and its object is to provide an optical information medium which is less susceptible to mar or flaw during the user's handling, and specifically, an optical information medium having a recording density increased due to the increased NA of a recording/reading optical system, which medium is less susceptible to mar or flaw by collision of a pickup during the recording and/or reading operation. Another object of the invention is to provide a method for evaluating the mar resistance of an optical information medium on its recording/reading light incident side surface, by quantitative determination in a state reflecting an actual service environment and in a simple way.

The above objects are attained by the present invention which is defined as (1) to (11) below.

(1) An optical information medium comprising a light-transparent substrate and an information recording layer, wherein optical recording and/or reading is performed with a laser beam that enters said information recording layer from the light-transparent substrate side, wherein said medium includes a cured polysilazane film disposed on the laser beam incident side of said light-transparent substrate, and said light-transparent substrate or said light-transparent substrate having the cured polysilazane film integrated thereon has a tensile modulus of at least 200 MPa.

(2) The optical information medium of (1) wherein said light-transparent substrate includes a resin layer of 30 to 300 $\mu$m thick.

(3) The optical information medium of (1) or (2) wherein said cured polysilazane film has a thickness of 0.2 to 50 $\mu$m.

(4) The optical information medium of any one of (1) to (3) wherein the laser beam incident side surface has a pencil hardness of at least HB.

(5) The optical information medium of any one of (1) to (4) wherein said cured polysilazane film is a laminate including a plurality of films of different compositions, in which a cured film of inorganic polysilazane and a cured film of organic group-introduced polysilazane are stacked in the described order when said cured polysilazane film is viewed from the laser beam incident side.

(6) The optical information medium of any one of (1) to (5) further comprising a functional layer on the laser beam incident side of said cured polysilazane film, said functional layer having at least one function selected from among lubricity, water repellency and oil repellency.

(7) The optical information medium of (6) wherein said functional layer has a thickness of up to 500 nm.

(8) The optical information medium of (6) or (7) wherein said functional layer is made of a compound having hydrolyzable silyl groups.

(9) In connection with an optical information medium comprising a light-transparent substrate and an information recording layer, wherein optical recording and/or reading is performed with a laser beam that enters said information recording layer from the light-transparent substrate side, a method for evaluating the optical information medium for mar resistance on its laser beam incident side surface, comprising the steps of intentionally abrading the laser beam incident side surface of the optical information medium; then measuring a recording/reading characteristic; and evaluating the mar resistance of the laser beam incident side surface on a basis of the measured value.

(10) The method of (9) wherein an abrasive wheel as prescribed by ISO 9352 is used as the means for intentionally abrading the laser beam incident side surface of the optical information medium.

(11) The method of (9) wherein #0000 steel wool is used as the means for intentionally abrading the laser beam incident side surface of the optical information medium.

FUNCTION AND EFFECT

Searching for a hard coat layer suitable for protecting the surface of a light-transparent substrate in an optical information medium, we have found that a film formed by curing polysilazane is appropriate for the purpose. Use of a cured polysilazane film as a protective layer on information media is described in the above-referred JP-A 2000-132865. It is noted that the Examples demonstrated therein are only those media in which a red sensitive layer of 0.2 $\mu$m thick containing a dye and a resin binder is formed on a polyethylene terephthalate support of 20 $\mu$m thick and a protective layer of polysilazane and 0.1 $\mu$m thick is formed on the red sensitive layer. It is described therein that the protective layer preferably has a dry film thickness of 0.001 to 0.2 $\mu$m, and more preferably 0.05 to 0.15 $\mu$m. The reason why the thickness of the protective layer is limited to this range is described nowhere.

In Examples demonstrated in the above publication, tape media are evaluated in the state accommodated in a cartridge. Since the tape medium does not contact any member other than the cartridge during handling, there is little chance for the tape medium to be marred. The above publication pays no attention to the collision of a pickup, which becomes a problem for optical disks. By contrast, most optical disks are of the type that disks are not accommodated in cartridges, and they are susceptible to mars and flaws on their laser beam incident side surface. Also, those optical disks applied to the recording/reading system with increased NA have an increased chance for a pickup to collide against the laser beam incident side surface. Therefore, the optical disk on its laser beam incident side surface is required to have improved abrasion resistance and mar resistance. Although the cured polysilazane film has a high hardness, the thickness of 0.1 $\mu$m described in the above-referred JP-A 2000-132865 is insufficient to provide the abrasion resistance and mar resistance required for the optical disk on its laser beam incident side surface.

However, it was empirically found that since the cured polysilazane film has increased internal stresses, forming the cured polysilazane film to an increased thickness invites a likelihood of self-destruction. Continuing experiments in order to prevent the cured polysilazane film from self-destruction, we have found that the likelihood of self-destruction depends on the tensile modulus of a light-transparent substrate underlying the cured polysilazane film. Then the present invention sets the tensile modulus of the light-transparent substrate in a specific range for making it possible to form the cured polysilazane film to a substantial thickness, eventually obtaining an optical information medium having satisfactory abrasion resistance and mar resistance on the laser beam incident side surface.

The evaluation method of the invention can evaluate the mar resistance of an optical information medium on its laser beam incident side surface, by quantitative determination in a state reflecting an actual service environment and in a simple way.

DESCRIPTION OF THE PREFERRED EMBODIMENTS

Optical Information Medium

The invention provides an optical information medium comprising a light-transparent substrate and an information recording layer, wherein optical recording and/or reading is performed with a laser beam that enters the information recording layer from the light-transparent substrate side. Illustrative constructions of the optical information medium are shown in FIGS. 1 and 2.

Figure 1:
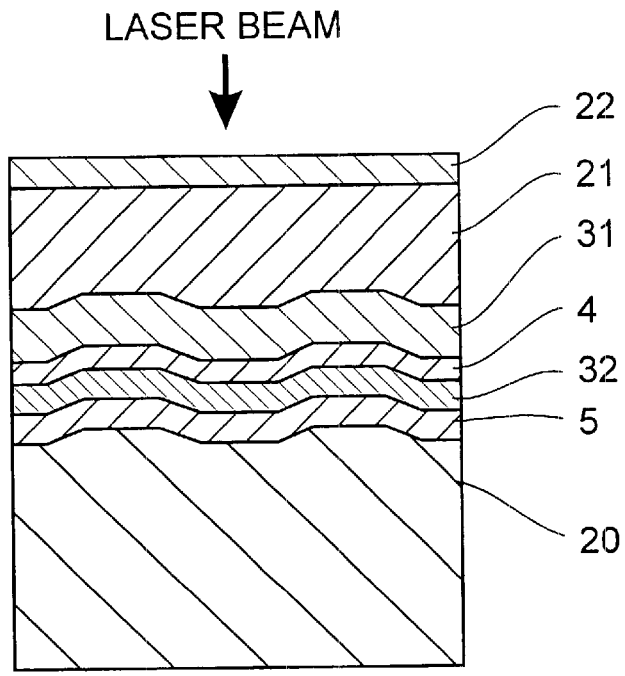
FIG. 1 is a fragmentary cross-sectional view of an optical information medium according to one embodiment of the invention.

The optical information medium of FIG. 1 is a recording medium of the phase change type and has a reflective layer 5, a second dielectric layer 32, a recording layer 4 serving as an information recording layer, a first dielectric layer 31, a light-transparent substrate 21 and a cured polysilazane film 22 formed in the described order on one surface of a supporting substrate 20. The light-transparent substrate 21 is a resin layer which is formed by joining a resin sheet or by coating a resin. A laser beam for recording and/or reading is transmitted by the light-transparent substrate 21 to the recording layer 4. The medium of the structure shown in FIG. 1 is compliant with the increased NA of the objective lens of the recording/reading optical system and thus suitable for high-density recording since the light-transparent substrate 21 can be made thin. In the structure shown in FIG. 1, the total thickness of the light-transparent substrate 21 and cured polysilazane film 22 is preferably 30 to 300 μm, and more preferably 30 to 200 μm. If the thickness is too thin, the optical influence of debris deposited on the laser beam incident side surface of the medium becomes substantial. If the thickness is too thick, it becomes difficult to achieve a high recording density due to increased NA.

Figure 2:
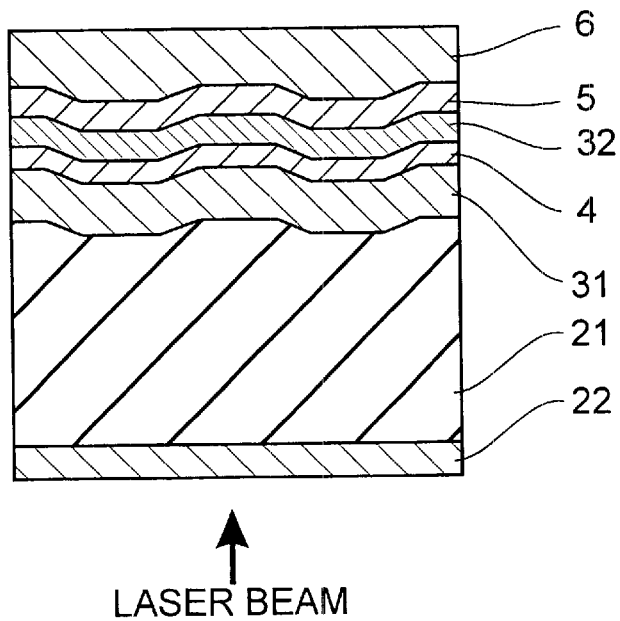
FIG. 2 is a fragmentary cross-sectional view of an optical information medium according to another embodiment of the invention.

The medium shown in FIG. 2 has a first dielectric layer 31, a recording layer 4, a second dielectric layer 32, a reflective layer 5, and a protective layer 6 formed in the described order on one surface of a light-transparent substrate 21 and a cured polysilazane film 22 formed on the other surface of the light-transparent substrate 21. In this structure, a relatively highly rigid light-transparent substrate 21 having a thickness of about 0.4 to 2 mm is used. In the structure shown in FIG. 2, the arrangement of the respective layers as viewed from the laser beam incident side is the same as in the medium of FIG. 1 except for the protective layer 6.

It is the structure shown in FIG. 2 that commercial optical disks such as DVD-RAM and DVD-RW employ. On the other hand, FIG. 1 shows the structure in which the lamination order of layers including a reflective layer and recording layer is inverse to FIG. 2. In this disclosure, the medium of the structure shown in FIG. 1 is referred to as the inverse laminate type.

The invention is applicable to any type of recording layer. More particularly, the invention is applicable not only to recording media of the phase change type as illustrated, but also to recording media of the pit formation type and magneto-optical recording media. The invention is not limited to the recordable type as illustrated, and is also applicable to the read only type. In such a case, rows of pits formed integral with the supporting substrate 20 and a reflective layer formed thereon constitute the information recording layer.

According to the invention, the cured polysilazane film 22 is disposed on the laser beam incident side of the light-transparent substrate 21 as illustrated in FIGS. 1 and 2. The cured polysilazane film 22 is comprised of silica originating from polysilazane or silica and polysilazane. Consequently, the cured polysilazane film 22 has a fully high hardness and excellent abrasion resistance and mar resistance. In the medium of the inverse laminate type shown in FIG. 1, there is an increased chance for the pickup to collide against the light-transparent substrate 21 to damage the substrate since the working distance is reduced due to the increased NA of the objective lens of the recording/reading optical system. In the inverse laminate type, flaws on the surface of the light-transparent substrate 21 have a substantial influence since the light-transparent substrate 21 is thin. Accordingly, the invention is especially suited for media of the inverse laminate type.

The cured polysilazane film 22 may be composed entirely of silica originating from polysilazane or silica and polysilazane, or have silica originating from polysilazane or silica and polysilazane dispersed or incorporated in its entirety.

Preferably the cured polysilazane film has a thickness of at least 0.05 μm, more preferably at least 0.2 μm, even more preferably at least 0.25 μm, and most preferably at least 0.5 μm. Too thin a cured polysilazane film fails to exert satisfactory abrasion resistant effects.

Because of increased internal stresses, the cured polysilazane film becomes more self-destructible as it becomes thicker. However, to obtain satisfactory medium protecting effects, the cured polysilazane film must be relatively thick. While the cured polysilazane film itself is consolidated to a high hardness, its medium protecting effects sometimes become insufficient, depending on the physical properties of the underlying light-transparent substrate 21. Then the invention prescribes that the light-transparent substrate 21 has a tensile modulus of at least 200 MPa, and preferably at least 400 MPa. As long as the tensile modulus of the light-transparent substrate 21 is in this range, the likelihood of self-destruction is minimized even when the cured polysilazane film 22 is relatively thick, specifically has a thickness of at least 0.2 μm, further at least 0.25 μm, and even at least 0.5 μm. It is understood that too thick a cured polysilazane film 22 yet becomes self-destructible. It is preferred that the cured polysilazane film 22 have a thickness of up to 50 μm, more preferably up to 10 μm, and even more preferably up to 5 μm. Also as long as the tensile modulus of the light-transparent substrate 21 is in the above-defined range, the cured polysilazane film 22 exerts fully high medium protecting effects. Specifically, the laser beam incident side surface where the cured polysilazane film 22 is disposed has a pencil hardness of at least HB. It is noted that the pencil hardness used herein is as prescribed by ISO/DIS 15184:1996.

Understandably, the cured polysilazane film 22 once formed on the light-transparent substrate 21 is difficult to peel therefrom, and it is thus difficult to measure the tensile modulus of the light-transparent substrate 21 after the cured polysilazane film 22 is formed thereon. However, since the cured polysilazane film 22 is extremely thin as compared with the light-transparent substrate 21, the tensile modulus of the light-transparent substrate 21 measured without removing the cured polysilazane film 22 does not substantially differ from that of the light-transparent substrate 21 alone. It is then acceptable herein that the tensile modulus of the light-transparent substrate 21 having the cured polysilazane film 22 integrated therewith is at least 200 MPa, and preferably at least 400 MPa.

No particular upper limit is imposed on the tensile modulus of the light-transparent substrate 21 or the tensile modulus of the light-transparent substrate 21 having the cured polysilazane film 22 integrated therewith. However, the upper limit of tensile modulus is usually about 3,000 MPa when the light-transparent substrate 21 is made of a commonly available material.

It is understood that the tensile modulus used herein is as prescribed by JIS K7127-1989. On measurement of tensile modulus, some parameters are set to:

specimen length: 60 mm, specimen width: 10 mm, distance between two gage marks: 40±1 mm, distance between two clamps: 44±1 mm, and pulling speed: 30 mm/min, and the remaining measurement conditions are in accord with JIS K7127-1989. These parameters are changed from JIS K7127-1989 because the size (usually diameter approx. 12 cm) of the medium (optical disk) is taken into account so that measurement may be made on the light-transparent substrate separated from the medium.

The cured polysilazane film 22 is formed by applying a polysilazane solution onto the laser beam incident side surface of the light-transparent substrate 21 and heating the coating for curing. It is known that when heat treated in the air, polysilazane undergoes hydrolysis with air-borne moisture to form dense silica of very high purity. If a metal catalyst is previously added to the polysilazane solution, the reaction readily proceeds even on heating at about 100° C., achieving conversion to high-purity silica. The heating temperature is preferably 25 to 130° C., more preferably 50 to 120° C. and the heating time is preferably 10 minutes to 10 hours, more preferably 10 minutes to 5 hours. Cure may not proceed to a full extent if the heating temperature is low or the heating time is short. It is noted that a coating of polysilazane can be cured by allowing it to stand at room temperature. The method of applying the polysilazane solution is not critical, and any of gravure coating, dip coating, spray coating and spin coating techniques may be employed.

The polysilazane used herein is any of conventional well-known polysilazanes which have Si—N—Si bonds. The preferred polysilazanes include cyclic inorganic polysilazanes and chain-like inorganic polysilazanes having a structure $(—Si(H)_2—NH—)_n$ wherein n is 100 to 50,000, mixtures thereof, and polyorganohydrosilazanes in which some or all of the hydrogen atoms attached to silicon atoms on the foregoing inorganic polysilazanes are substituted with organic groups. Also included are polysiloxazanes containing oxygen in the molecule, polymetalosilazanes produced by reaction with metal alkoxides or the like, and polyborosilazanes produced by reaction with organic boron compounds. Commercially available polysilazane solutions, for example, N-L110 (Tonen General Oil Co., Ltd.) are also useful.

The cured polysilazane film may be a laminate of a plurality of films having different compositions. The cured product of inorganic polysilazane itself has a very high hardness, although a thickness beyond a certain level is necessary to endow its film with a fully high hardness. However, an attempt to form a thick film from inorganic polysilazane leads to the likelihood of self-destruction. On the other hand, the cured product of polysilazane having organic groups introduced therein, though its own hardness is somewhat low, eliminates the likelihood of self-destruction even in the form of a thick film. With this borne in mind, a cured film of polysilazane having organic groups introduced therein is formed relatively thick as a underlying layer, a cured film of inorganic polysilazane is formed thereon relatively thin as a surface layer, and the resulting laminate film as a whole has a satisfactory thickness and hence, a fully high hardness. Additionally, the laminate film has a fully high surface hardness. To achieve a fully high surface hardness in this embodiment, the cured film of inorganic polysilazane should preferably have a thickness of at least 0.05 $\mu$m and more preferably at least 0.2 $\mu$m.

The cured polysilazane film has a very high hardness since it is based on dense silica of high purity. Since hydrogen atoms attached to silicon atoms and nitrogen atoms in polysilazane act as active hydrogen, the cured film of polysilazane has dramatically improved adhesion to the surface of the light-transparent substrate 21. It is acceptable herein that polysilazane is partly left in the cured polysilazane film without being converted to silica. When polysilazane having organic groups introduced therein is used, organic groups are generally present in the cured polysilazane film as well.

Examples of the solvent used in preparing the polysilazane solution include aromatic hydrocarbon solvents such as benzene, toluene and xylene, ethers, tetrahydrofuran, methylene chloride, and carbon tetrachloride. It is noted that when the polysilazane solution is directly applied to the surface of the light-transparent substrate 21, a choice must be made of the solvent that does not attack the material of which the light-transparent substrate 21 is made. The material of which the light-transparent substrate 21 is made is preferably polycarbonate, and the solvent that does not attack polycarbonate and can be used as a dilution solvent for polysilazane is selected, for example, from ether solvents such as dibutyl ether.

The light-transparent substrate 21 is a resin layer in the inverse laminate type shown in FIG. 1 and a relatively rigid plate member in the structure shown in FIG. 2. The light-transparent substrate 21 in FIG. 1 can be formed, for example, by joining a resin sheet or by coating a resin. It can also be formed by joining a resin sheet and further applying a resin thereon or by stacking a plurality of resin coatings. The light-transparent substrate 21 in FIG. 2 can be formed, for example, by injection molding or the photo-polymer (2P) method.

The light-transparent substrate 21 is preferably made of thermoplastic resins such as polycarbonate and polymethyl methacrylate (PMMA) and actinic radiation-curable resins such as UV-curable acrylic resins. In the structure shown in FIG. 2, the light-transparent substrate 21 may be made of glass and a pattern of grooves or pits be formed on its surface by the 2P method.

Figure 3:
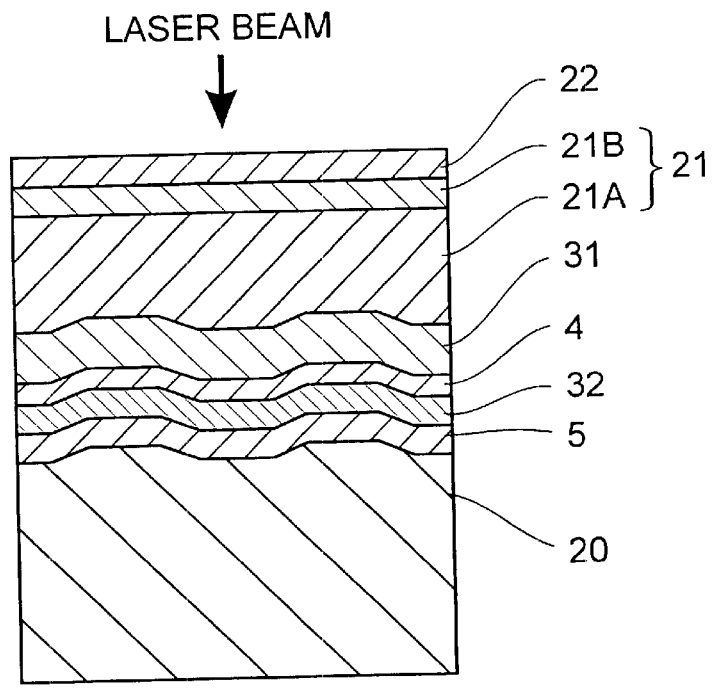
FIG. 3 is a fragmentary cross-sectional view of an optical information medium according to a further embodiment of the invention.
Figure 4:
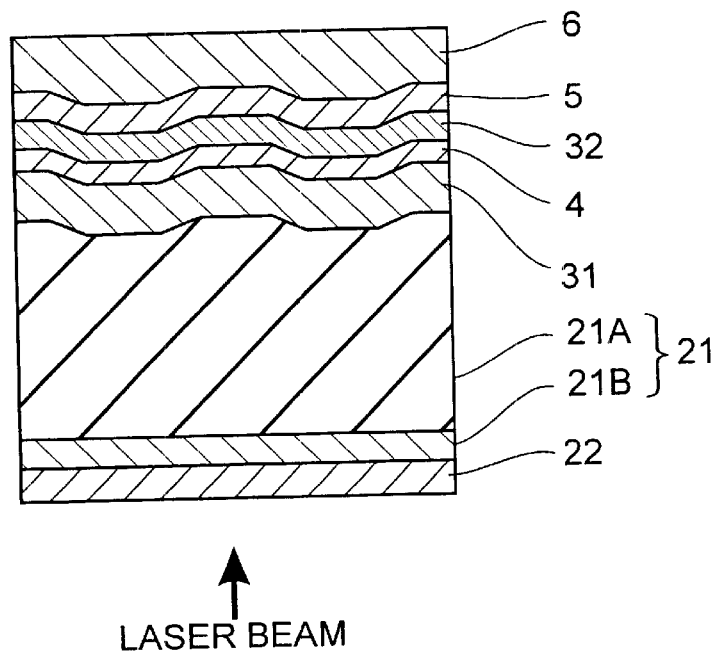
FIG. 4 is a fragmentary cross-sectional view of an optical information medium according to a further embodiment of the invention.

The light-transparent substrate 21 may be composed of a plurality of layers of different constituent materials. FIGS. 3 and 4 show media in which the light-transparent substrate 21 has a laminate structure consisting of a substrate body 21A and a barrier layer 21B and the remaining components are the same as in the structures of FIGS. 1 and 2. The barrier layer 21B is disposed between the substrate body 21A and the cured polysilazane film 22 and serves to protect the substrate body 21A from the coating solvent when the polysilazane solution is applied. For example, since xylene typical of the organic solvent attacks polycarbonate, it is prohibited to use xylene as the coating solvent for the formation of the cured polysilazane film when the light-transparent substrate 21 in the structure shown in FIG. 1 is a resin sheet of polycarbonate. In contrast, the use of xylene as the coating solvent is permissible in the structure shown in FIG. 3 wherein the substrate body 21A is made of a polycarbonate sheet and the barrier layer is made of a resin resistant to xylene attack, for example, an actinic radiation-curable resin such as an acrylic resin, affording a higher freedom of choice for the coating solvent.

The material of which the barrier layer 21B is made is not critical and may be selected, as appropriate for a particular type of coating solvent, from among actinic radiation-curable resins such as UV-curable resins, the foregoing resins having colloidal silica dispersed therein, and inorganic thin films such as $SiO_2$ film formed by sputtering.

The thickness of the barrier layer may be set so as to provide a sufficient protective effect to the coating solvent and is generally selected in the range of 50 nm to 200 $\mu$m and in the range of 50 nm to 10 $\mu$m for the inverse laminate type having a thin light-transparent substrate 21 as shown in FIG. 3.

It is understood that the light-transparent substrate 21 of the laminate structure is not limited to the above embodiment wherein the barrier layer is provided. The laminate structure may be employed for controlling the physical properties of the light-transparent substrate 21, as in a case wherein a relatively soft layer and a relatively hard layer are stacked in order to endow the light-transparent substrate 21 with both good optical properties and high strength.

If necessary, the surface underlying the cured polysilazane film, that is, the surface of the light-transparent substrate 21 is modified by plasma or corona discharge treatment or treatment with high-energy radiation such as UV radiation. In one appropriate procedure employed where the underlying portion is formed of an actinic radiation-curable resin, the exposure dose of actinic radiation is properly controlled so that the polymerization reaction of the underlying portion is interrupted, the polysilazane solution is applied to the underlying surface, and thereafter, actinic radiation is irradiated again to drive the polymerization reaction of the underlying portion to completion. Any of the above treatments is effective for improving the adherence between the cured polysilazane film and the underlying surface and eventually, further increasing the surface hardness of the cured polysilazane film.

Figure 5:
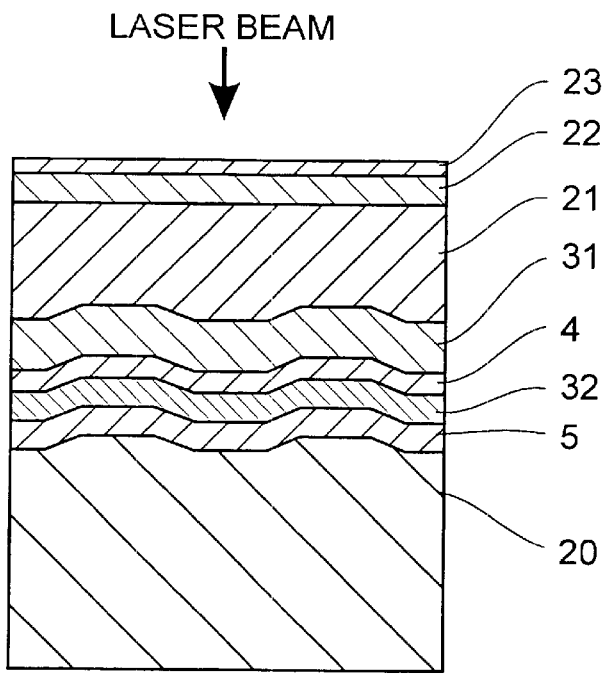
FIG. 5 is a fragmentary cross-sectional view of an optical information medium according to a further embodiment of the invention.
Figure 6:
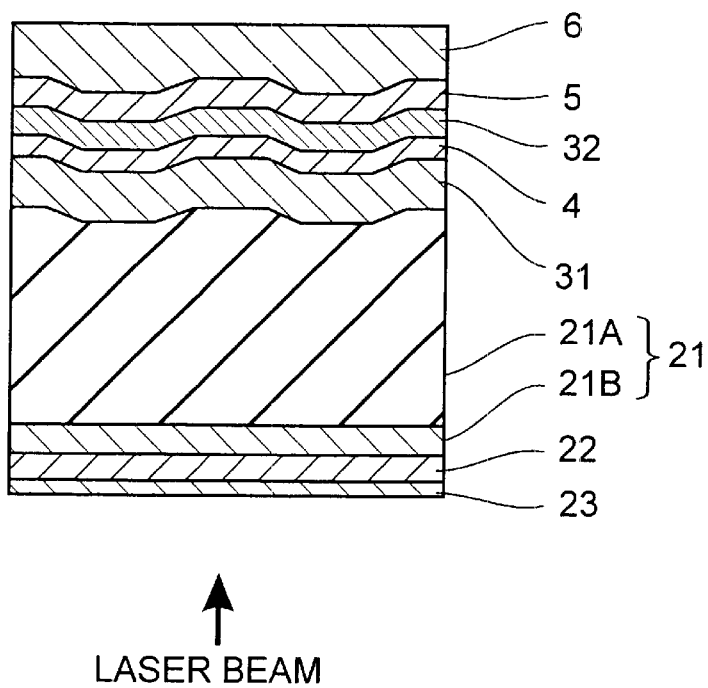
FIG. 6 is a fragmentary cross-sectional view of an optical information medium according to a further embodiment of the invention.

Although the cured polysilazane film by itself can establish very high abrasion resistance, another layer may be provided on the surface of the cured polysilazane film. The other layer is preferably a functional layer having at least one function selected from lubricity, water repellency and oil repellency. FIGS. 5 and 6 show media in which a functional layer 23 is disposed on the surface of the cured polysilazane film 22 while the remaining components are identical with the structures shown in FIGS. 1 and 4, respectively. For example, when the cured polysilazane film 22 is covered on the surface with a functional layer 23 having lubricity, the abrasion resistance and the resistance against pickup collision of the surface are further enhanced. Also when the cured polysilazane film 22 is covered on the surface with a functional layer 23 having water or oil repellency, contaminants are unlikely to deposit or readily wiped off if deposited.

The surface of the functional layer with lubricity preferably has a coefficient of dynamic friction of up to 0.4, and more preferably up to 0.3, as prescribed by ISO 8295:1995. It is noted that on measurement, a smooth glass plate is used as the contacting object. The lower limit of coefficient of friction is not critical although it is usually difficult to reduce the coefficient of friction below 0.03. On the other hand, the water or oil repellency of a material is definitely represented by the critical surface tension ($\gamma_c$/mNm$^{-1}$) which is a measure of surface free energy of the material. The critical surface tension can be determined from a measurement of contact angle. The contact angle ($\theta$/rad) of a smooth material surface is measured on several saturated hydrocarbon liquids each having a known surface tension ($\gamma_1$/mNm$^{-1}$), and the value obtained by extrapolating cos $\theta$=1 in the cos $\theta$ versus $\gamma_1$ plot is $\gamma_c$. In order that a certain material repel a liquid, $\gamma_c$ of the material must be below the surface tension $\gamma_1$ of the liquid.

The material of which the functional layer is made may be any of commonly used materials. Illustrative examples include higher fatty acid esters and derivatives thereof such as butyl stearate and butyl myristate, silicone fluids and modified ones thereof as typified by dimethylsiloxane derivatives, and fluorinated hydrocarbon lubricants and derivatives thereof. Since the functional layer is disposed on the surface of the cured polysilazane film, it is also preferred that the functional layer be formed of silane coupling agents based on fluorinated hydrocarbons. These silane coupling agents generally have the structure in which hydrolyzable silyl groups are bonded to fluorinated hydrocarbon chains. Since the silyl groups form strong chemical bonds with the surface of the cured polysilazane film through hydrolytic reaction, the functional layer of the silane coupling agent is highly durable. In the practice of the invention, a proper choice may be made among these materials, and a material having two or more functions selected from lubricity, water repellency and oil repellency is also useful. The material having lubricity, water repellency and oil repellency is disclosed, for example, in JP-A 11-213444 and JP-A 6-187663.

The functional layer preferably has a thickness of up to 500 nm, and more preferably up to 100 nm. If the functional layer is too thick, there is a risk that the hardness of the medium surface does not reflect the surface hardness of the cured polysilazane film and a concern about detracting from the optical transparency of the functional layer. The thickness of the functional layer should preferably be at least 1 nm in order for the layer to fully exert such functions as lubricity, water repellency and oil repellency.

Evaluation of Optical Information Medium

Described below is the method for evaluating the optical information medium for mar resistance on its recording/reading light incident side surface.

Making extensive investigations on the correlation of the degree of abrasion of a light-transparent substrate whose surface is abraded by various methods to the recording/reading characteristics of an optical information medium after abrasion of the light-transparent substrate, the inventors found that a relatively strong correlation exists between the degree of abrasion of a light-transparent substrate and the reflectance, jitter or error rate upon recording/reading after abrasion.

Specifically, when an appropriate abrasion technique is selected, the reflectance, jitter and other characteristics of an optical information medium are represented as a function of abrasion conditions such as abrasion time. Accordingly, the evaluation method of the invention can quantitatively determine the abrasion resistance and mar resistance of a light-transparent substrate in an actual optical information medium by intentionally abrading the light-transparent substrate surface of the optical information medium by a selected abrasion technique, then evaluating a reflectance or an electric characteristic such as jitter or error rate.

In the evaluation of the light-transparent substrate of the medium, the technique used to intentionally abrade the surface and the means used for abrasion are not critical as long as abrasion occurs in a reproducible manner. However, since a longer time taken for evaluation is undesirable, it is desirable to employ an abrasion technique and means capable of causing abrasion to a greater extent than the abrasion that can occur in an actual service environment of optical information media, by abrading operation within about 1 to 60 minutes, more preferably within about 1 to 30 minutes.

Illustrative, preferred abrasion techniques include the standardized test procedures such as the abrasion test procedure using abrasive wheels prescribed by ISO 9352 and the abrasion test procedure using abrasives prescribed by JIS K7205, and a technique of abrading with steel wool.

The abrasion test procedure using abrasive wheels prescribed by ISO 9352 is a test procedure commonly known as Taber abrasion test and is carried out as follows. The procedure uses an abrader in which two abrasive wheels are disposed at predetermined positions on a turntable. A sample is rested on the turntable. A predetermined load is applied to the abrasive wheels and the turntable is rotated by a motor. During rotation, the abrasive wheels abrade the sample surface while maintaining a certain tilt to the rotational direction of the turntable. There are furnished several sets of abrasive wheels which differ in material and abrasive grain size. By properly selecting the type of abrasive wheels, the load applied during abrading operation, and the revolution of the turntable, the abrasion resistance of the sample can be ascertained. For general hard coat layers in optical information media, it is preferred to abrade them by using elastic abrasive wheels selected from CS-10, CS-10F and CS-17, and rotating the turntable over 10 to 500 cycles under a load of 2.5 N to 9.8 N.

The abrasion procedure using steel wool generally involves using #0000 steel wool for polishing, pressing it against the sample under a predetermined weight, and moving back and forth predetermined strokes.

Among the above test procedures, the abrasion test procedure using abrasive wheels is most preferable because it can be applied to a relatively wide variety of materials by selecting the type of abrasive wheels and the applied load, and it is the internationally standardized test procedure. Notably, the abrasion procedure using steel wool is also useful because it requires no special instrument and is simple.

In the method commonly used in the prior art, the degree of abrasion of the sample abraded by any of the above abrasion test procedures is most often quantitatively determined as a change of any of various parameters such as the thickness and weight of the sample, and optical scattering. According to the evaluation method of the invention, the optical information medium as abraded is directly evaluated by means of an optical disk drive unit.

In the evaluation method of the invention, the recording/reading characteristics selected as an item of evaluation are not particularly limited and include, for example, the reflectance, modulation or RF signal flatness during medium reading operation; jitter, output level, carrier-to-noise (CN) ratio or error rate of any one of recorded signals, overwritten signals, and once written signals; and a peak-to-peak (p-p) value of a focusing sensitivity curve at the linear velocity during recording or reading operation, the quantity of residual errors in focusing error signals, or the ratio of the p-p value to the quantity of residual errors. One or more of these are selected as an item of evaluation and measured. It is noted that the focusing sensitivity curve is generally referred to as S-curve and described, for example, in Optical Disk Technology, Radio Technology K.K., Feb. 10, 1989, page 81. From the focusing sensitivity curve, the p-p value of focusing error signal output, that is, the difference between the peak value of positive side output and the peak value of negative side output is determined and designated F, and the output p-p value of residual error component in focusing error signals is determined and designated R. If R/F is low, and specifically 10% or lower, the jitter on reading is fully small and writing errors are fully reduced.

The optical information medium to which the evaluation method of the invention is applicable is not critical as long as the medium has a light-transparent substrate and an information recording layer, wherein a laser beam for recording and/or reading enters the information recording layer through the light-transparent substrate, that is, the same construction as the above-described optical information medium of the invention.

EXAMPLE

Illustrative examples of the invention are given below. The invention is not limited to the examples illustrated below. Comparative examples are also described.

Example 1

Inverse Laminate Type

Medium 1

Medium 1 having the same structure as FIG. 1 except that it was of the read only type was fabricated by the following procedure.

First, a polycarbonate substrate (outer diameter 120 mm, thickness 1.2 mm) in the surface of which random signal data were previously formed as prepits was used as a supporting substrate 20. On the surface of the supporting substrate 20 where prepits were formed, a reflective layer of aluminum was deposited to a thickness of 100 nm by a sputtering technique. Then a coating of UV-curable resin (SD301 by Dainippon Ink & Chemicals, Inc.) was applied to a thickness of 100 $\mu$m by a spin coating technique and cured with UV radiation to form a light-transparent substrate 21. It is noted that when the light-transparent substrate 21 after curing was peeled from the reflective layer and measured for tensile modulus, it had a tensile modulus of 970 MPa.

Next, on the light-transparent substrate 21, a xylene solution of inorganic polysilazane (N-L110 by Tonen General Oil Co., Ltd., solids concentration 20% by weight) was applied by a spin coating technique, allowed to stand for one minute at room temperature, and heated at 100° C. for 30 minutes for curing, forming a cured polysilazane film 22. The cured polysilazane film 22 had a thickness of 0.2 $\mu$m. In this Medium 1, signals are read by irradiating a laser beam to the reflective layer from the cured polysilazane film 22 side.

In this medium, the laser beam incident side surface had a pencil hardness of H.

Medium 2 (Comparison)

Medium 2 was fabricated as was Medium 1 except that the cured polysilazane film was omitted. In this medium, the laser beam incident side surface had a pencil hardness of B.

Medium 3

Medium 3 having the same structure as FIG. 5 except that it was of the read only type was fabricated. Medium 3 corresponded to Medium 1 in which a functional layer 23 of silicone fluid (KF96 by Shin-Etsu Chemical Co., Ltd., viscosity 10,000 cp) was formed on the surface of the cured polysilazane film 22 to a thickness of about 100 nm by a spin coating technique. The functional layer 23 on its surface had a coefficient of friction of 0.25 as measured according to ISO 8295:1995. The pencil hardness of the laser beam incident side surface remained unchanged despite the provision of the functional layer 23.

Evaluation

Each of the above media was mounted on an optical disk drive unit where the bit error rate (BER) of read signals was measured. The optical disk drive unit used for evaluation had a laser wavelength of 650 nm. Next Medium 1 was set on a Taber abrader and abraded by using abrasive wheels CS-10F and a load of 4.9 N and rotating the turntable 10 revolutions. The BER after abrasion was similarly measured. Thereafter, this disk was further abraded by using the above abrasive wheels and rotating the turntable further 40 revolutions (total 50 revolutions) whereupon the BER was similarly measured. BER is correlated to the generation of flaw such that the flaw generated increases BER. The BER at the initial, after 10 cycles of abrasion and after 50 cycles of abrasion is rated "O" when it is less than $1.0 \times 10^{-4}$ and "×" when it is $1.0 \times 10^{-4}$ or more. The results are shown in Table 1.

To evaluate the influence of a pickup colliding against the medium during reading operation, the instrument DDU-1000 by Pulstec Industry K.K. was modified so that the pickup might intentionally contact the medium during rotation. While the medium was rotated at a fixed linear velocity (6.0 m/s), the pickup was contacted with the medium at a radius of 40 mm and kept in sliding motion for 3 minutes. Thereafter, focusing error signals were inspected to ascertain whether or not the waveform was disturbed before and after the sliding of the pickup. The rating was "⊚" when no change of focusing error signal was observed, "○" when some disturbance of signal was observed, and "×" when the focusing error signal contained substantial noise. The results are shown in Table 1. It is noted that the portion that comes in contact with the disk surface in this test is a lens protector made of polypropylene.

TABLE 1

|  | Cured |  | BER |  |  |  |
|---|---|---|---|---|---|---|
| | Barrier layer | polysilazane film | Functional layer | Initial | 10 cycles of abrasion | 50 cycles of abrasion | Focusing error signal |
| Medium 1 | — | formed | — | ○ | ○ | ○ | ○ |
| Medium 2 (comparison) | — | — | — | ○ | x | x | x |
| Medium 3 | — | formed | Formed | ○ | ○ | ○ | ⊚ |

As is evident from Table 1, Medium 1 having the cured polysilazane film was little flawed and did not detract from BER even when it was abraded. In contrast, Medium 2 not having the cured polysilazane film markedly detracted from BER, indicating poor abrasion resistance. By the contact and sliding of the pickup, Medium 1 undergoes a little signal disturbance whereas Medium 2 generated substantial noise. Medium 3 having the functional layer of silicone fluid experienced less disturbance of focusing error signal than Medium 1 after the sliding of the pickup.

Next, Medium 1A was fabricated as was Medium 1 except that the cured polysilazane film was formed by the following procedure. In Medium 1A, a cured film of polysilazane having organic groups introduced therein (N-L710 by Tonen General Oil Co., Ltd.) was first formed on the light-transparent substrate 21 to a thickness of 1 μm. Next, a cured film of inorganic polysilazane was formed on the cured film to a thickness of 0.2 μm, as in Medium 1. The laser beam incident side surface of Medium 1A had a pencil hardness equal to that of Medium 1. Medium 1A and Medium 1 were tested as above using a Taber abrader. To make the test conditions more rigorous, the turntable was rotated 100 revolutions. As a result, the BER after abrasion was at least $1.0 \times 10^{-4}$ for Medium 1, but less than $1.0 \times 10^{-4}$ for Medium 1A, confirming the effects of making the cured polysilazane film thicker.

Also, Medium 1B was fabricated as was Medium 1A except that the light-transparent substrate 21 was constructed of a UV-curable resin layer having a tensile modulus of 150 MPa. In Medium 1B, the cured polysilazane film underwent self-destruction or cracking.

Further, Medium 1C was fabricated as was Medium 1 except that the cured polysilazane film 22 had a thickness of 0.5 μm. Medium 1C was tested under the same conditions as was Medium 1A, obtaining equivalent results to Medium 1A. Moreover, Medium 1D was fabricated as was Medium 1C except that the light-transparent substrate 21 was constructed of a UV-curable resin layer having a tensile modulus of 150 MPa. In Medium 1D, the cured polysilazane film underwent self-destruction or cracking.

Example 2

Medium 4

A commercially available DVD-RAM (recording capacity 2.6 GB/side) was furnished. DVD-RAM is a phase change recording medium and has substantially the same structure as the medium shown in FIG. 2, two of which are joined together with the protective layers 6 abutted. The recording layer 4 is composed mainly of Ge, Sb and Te and the light-transparent substrate 21 was a polycarbonate substrate of 0.6 mm thick.

Using this DVD-RAM, Medium 4 having the structure shown in FIG. 4 was fabricated by the following procedure.

With the polycarbonate substrate of DVD-RAM being regarded substrate body 21A, a UV-curable acrylic resin (HOD-3200 by Nippon Kayaku Co., Ltd.) was applied on its laser beam incident side surface by a spin coating technique and cured by irradiating UV radiation (high-pressure mercury lamp, dose 300 mJ/cm$^2$), forming a barrier layer 21B of 3.3 μm thick. The light-transparent substrate 21 had a tensile modulus of 1,340 MPa.

Subsequently, a cured polysilazane film 22 was formed on the surface of the barrier layer 21B as in Medium 1. Then, 1.0 J/cm$^2$ of UV radiation was irradiated to the barrier layer 21B through the cured polysilazane film 22 for completely curing the barrier layer 21B. The laser beam incident side surface of this medium had a pencil hardness of H.

Random signals were recorded in a region of Medium 4 extending from 39.5 mm to 57.5 mm in radius whereupon the same tests as Medium 1 were carried out, finding good results equivalent to those of Medium 1. The results of focusing error signal after the pickup sliding are shown in Table 2.

Medium 5 (Comparison)

Medium 5 was fabricated as was Medium 4 except that the cured polysilazane film 22 was omitted and the dose of UV radiation irradiated during formation of the barrier layer 21B was 1.0 J/cm$^2$. The laser beam incident side surface of this medium had a pencil hardness of 2B.

The same tests as Medium 4 were carried out on Medium 5, finding results equivalent to those of Medium 2 without the cured polysilazane film and apparently inferior to those of Medium 4. The results of focusing error signal after the pickup sliding are shown in Table 2.

Medium 6

Medium 6 having the structure shown in FIG. 6 was fabricated. Medium 6 corresponded to Medium 4 in which a functional layer 23 of about 10 nm thick was formed on the surface of the cured polysilazane film 22. The functional layer 23 was formed by applying a 0.1 wt % perfluorohexane solution of water and oil repellent silane coupling agent (DSX by Daikin Industries, Ltd.) by a spin coating technique and heating at 60° C. for 10 hours in the air for chemical adsorption.

The functional layer 23 on its surface had a coefficient of friction of 0.20 as measured according to ISO 8295:1995. The functional layer 23 on its surface had a contact angle of 114.0° with water and 63.8° with n-hexadecane. The pencil hardness of the laser beam incident side surface remained unchanged despite the provision of the functional layer 23.

This medium was tested as was Medium 1. The BER after abrasion was as good as that of Medium 4. The focusing error signal after the pickup sliding are shown in Table 2, confirming noise reduction as compared with Medium 4. On the surface of Medium 6, stains such as fingerprints were unlikely to stick or readily wiped off if stuck.

TABLE 2

|  | Barrier layer | Cured polysilazane film | Functional layer | Focusing error signal |
|---|---|---|---|---|
| Medium 4 | formed | formed | — | ◯ |
| Medium 5 (comparison) | formed | — | — | x |
| Medium 6 | formed | formed | formed | ⊙ |

Media were fabricated as was Medium 4 except that the cured polysilazane film 22 was formed by the same procedures as Media 1A and 1C in Example 1. These media exhibited excellent abrasion resistance like Media 1A and 1C.

For Medium 6 and Medium 3 in Example 1, dry fabric (Bemcot Lint-Free CT-8 by Asahi Chemical Co., Ltd.) was slid 20 strokes on the surface of the functional layer 23. The load applied during the sliding was about 10 N. Before and after sliding, the functional layer 23 on the surface was measured for contact angle with water. The contact angle of Medium 3 was 98.3° before sliding and 83.5° after sliding, indicating that the silicone fluid was noticeably wiped off with the fabric. The contact angle of Medium 6 was 114.0° before sliding and 112.5° after sliding, indicating that the silane coupling agent was resistant to wiping off.

Example 3

Medium 7

Medium 7 having the same structure as FIG. 6 except that it was of the read only type was fabricated by the following procedure.

First, a polycarbonate substrate (outer diameter 120 mm, thickness 0.6 mm) in the surface of which random signal data were previously formed as prepits was used as a substrate body 21A. On the surface of the substrate body 21A remote from the prepitted surface, a barrier layer 21B was formed as in Medium 4. The light-transparent substrate 21 had a tensile modulus of 1,340 MPa. Subsequently a cured polysilazane film 22 was formed on the surface of the barrier layer 21B as in Medium 1.

On the prepitted surface of the substrate, a reflective layer of aluminum (100 nm thick) was deposited by a sputtering technique. Then a prepit-free polycarbonate substrate (outer diameter 120 mm, thickness 0.6 mm) was joined to the surface of the reflective layer with a UV-curable adhesive (acrylic, adhesive layer after curing had a thickness of 5.0 μm), completing an optical disk. This is designated Medium 7. In Medium 7, signals are read by transmitting a laser beam to the reflective layer from the surface of the cured polysilazane film.

Medium 7 was tested as was Medium 1, obtaining equivalent results to Medium 1. Media were fabricated as was Medium 7 except that the cured polysilazane film 22 was formed by the same procedures as Media 1A and 1C in Example 1. These media exhibited excellent abrasion resistance like Media 1A and 1C.

Medium 8 (Comparison)

Medium 8 was fabricated as was Medium 7 except that the cured polysilazane film 22 was omitted and the dose of UV radiation irradiated during formation of the barrier layer was 1.0 J/cm$^2$. In Medium 8, signals are read by transmitting a laser beam to the reflective layer from the surface of the barrier layer.

The same tests as Medium 1 were carried out on Medium 8, finding results equivalent to those of Medium 2 without the cured polysilazane film and apparently inferior to those of Medium 7.

Example 4

Evaluation of Mar Resistance

Sample No. 1

An optical recording disk sample of the structure shown in FIG. 4 was fabricated by the following procedure.

First, a grooved disk-shape substrate (made of polycarbonate, diameter 120 mm, thickness 0.6 mm) was used as a substrate body 21A of a light-transparent substrate 21. On the non-grooved surface of the substrate body 21A, a barrier layer 21B was formed as in Medium 7. Subsequently a cured polysilazane film 22 was formed on the surface of the barrier layer 21B as a hard coat layer. The groove depth was 18 nm and the recording track pitch was 0.74 μm.

Next, on the grooved surface of the light-transparent substrate 21, a first dielectric layer 31 of two-layer structure was formed by a sputtering technique. Of the two layers, the layer disposed adjacent the light-transparent substrate 21 had a composition of 80 mol % ZnS and 20 mol % SiO$_2$ and a thickness of 80 nm, and the layer disposed adjacent a recording layer 4 had a composition of 50 mol % ZnS and 50 mol % SiO$_2$ and a thickness of 5 nm.

Next, using an alloy target of phase change material, the recording layer 4 of 18 nm thick was formed by a sputtering technique. The recording layer 4 had a composition (atomic ratio) of $Sb_{74}Tb_{18}Ge_7In_1$.

Next, using a target of 50 mol % ZnS and 50 mol % SiO$_2$, a second dielectric layer 32 of 19 nm thick was formed by a sputtering technique.

Next, a reflective layer 5 of $Al_{98}Cr_2$ (atomic ratio) was formed by a sputtering technique.

Next, a UV-curable resin (SK5110 by Sony Chemical Co., Ltd.) was applied by a spin coating technique and exposed to UV radiation, forming a protective layer 6 of 5 μm thick. Thereafter, a dummy substrate of polycarbonate (diameter 120 mm, thickness 0.6 mm) was joined to the protective layer with a UV-curable adhesive, completing an optical recording disk sample.

Sample No. 2

Instead of the cured polysilazane film, a hard coat layer was formed by applying a UV-curable resin (SD318 by Dainippon Ink & Chemicals Inc.) by a spin coating technique and curing so as to give a thickness of 2.5 μm. The barrier layer was omitted. Otherwise like sample No. 1, an optical recording disk sample was fabricated.

Sample No. 3

An optical recording disk sample was fabricated like sample No. 1 except that the barrier layer and the hard coat layer were omitted.

Evaluation

The recording layer of each of the above-prepared samples was initialized or crystallized by means of a bulk eraser and then mounted on an optical recording medium tester where the reflectance of unrecorded portion was measured under the conditions:

laser wavelength: 650 nm, laser power: 1.0 mW, objective lens NA: 0.60, and linear velocity: 3.5 m/s, while tracking the groove. Next, 1–7 modulation signals (shortest signal length 2T) were recorded in the groove before the output level and jitter of read signals were measured. The results are shown in Table 3. It is noted that the jitter was determined by measuring read signals by means of a time interval analyzer (Yokogawa Electric Corp.) to determine a "signal fluctuation ($\sigma$)" and calculating according to $\sigma$/Tw (%) wherein Tw is the window margin. If the jitter is 13% or less, errors fall within the permissible range. To provide various margins in a satisfactory range, it is desired that the jitter be 10% or less, and more desirably 9% or less.

Next, each of the above samples was set on a Taber abrader where the laser beam incident side surface of the sample was abraded using abrasive wheels CS-10F under a load of 4.9 N. The number of abrasion cycles (number of revolutions of the turntable) is shown in Table 3. Thereafter, the reflectance of the unrecorded portion in the abraded area was similarly measured as well as the output level and jitter of signals recorded prior to abrasion. The results are shown in Table 3. It is noted that the output level in Table 3 is a relative value normalized based on a value of 100 prior to abrasion. Table 3 also shows percent drops of the reflectance and output level after abrasion from the reflectance and output level prior to abrasion, respectively.

Figure 7:
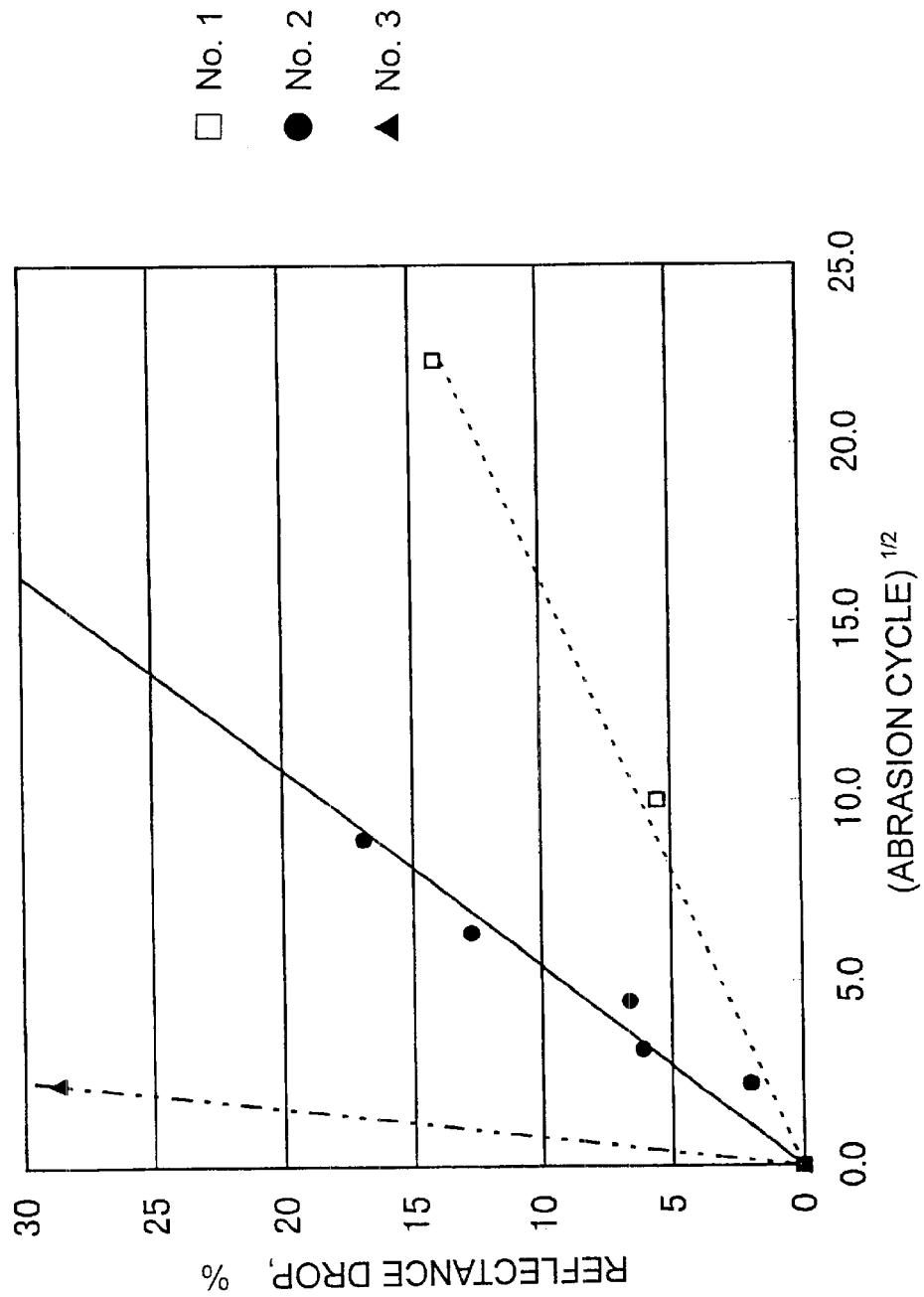
FIG. 7 is a graph showing a percent drop of the reflectance of media versus the number of abrasion cycles.
Figure 8:
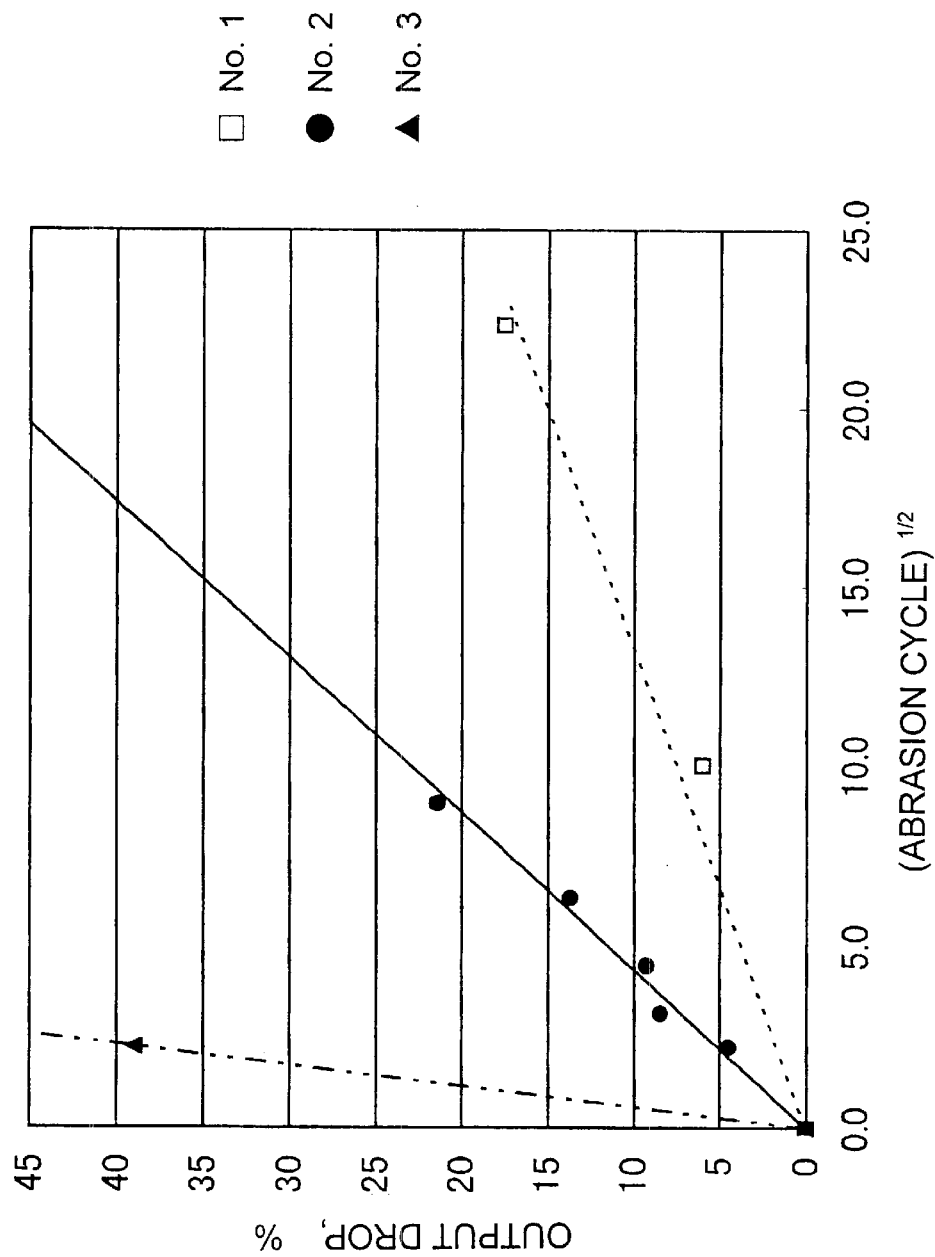
FIG. 8 is a graph showing a percent drop of the read output level from media versus the number of abrasion cycles.
Figure 9:
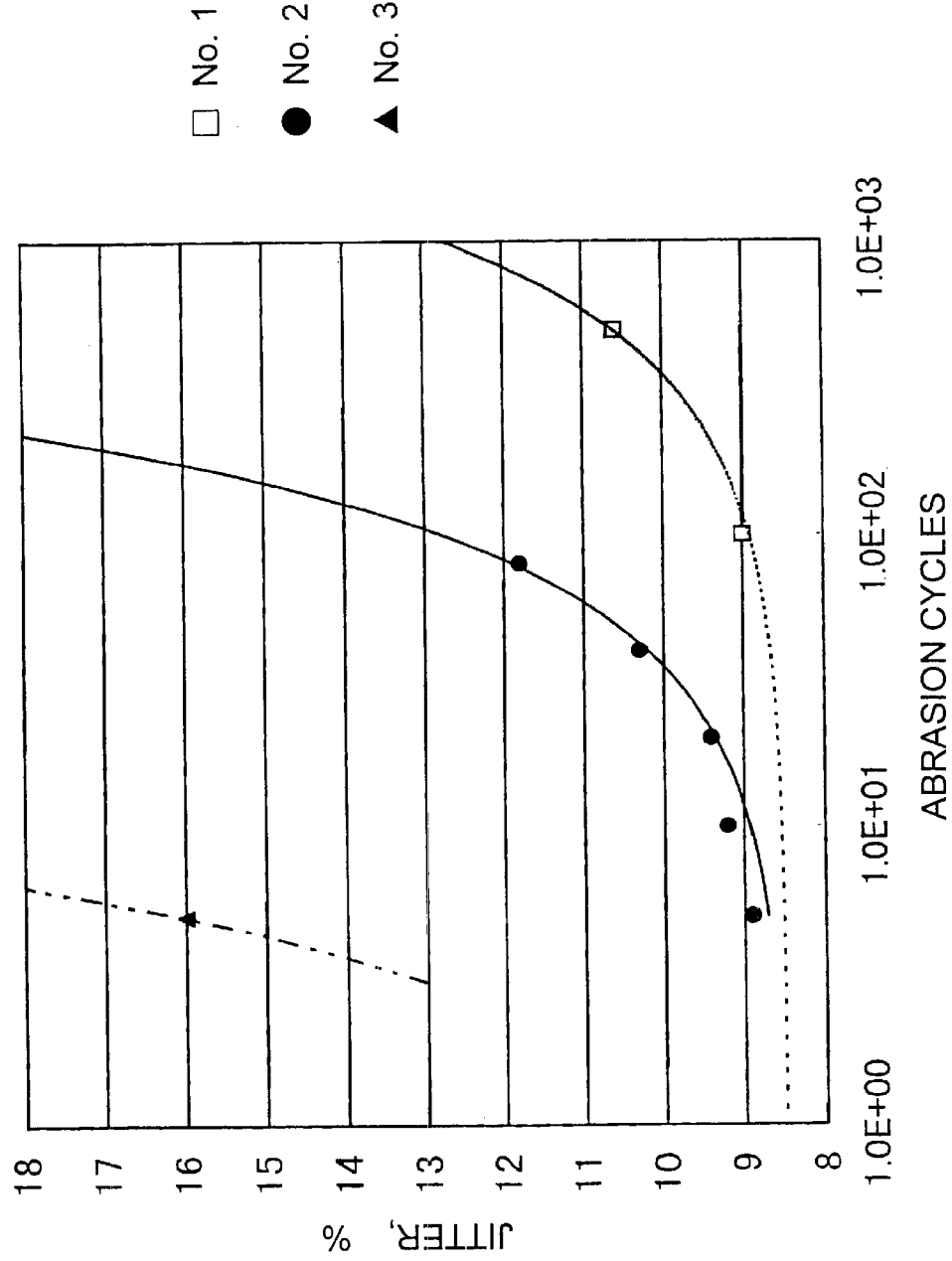
FIG. 9 is a graph showing the jitter of media versus the number of abrasion cycles.

Of the measured data shown in Table 3, the percent drop of reflectance, the percent drop of output level and the jitter are plotted relative to the number of abrasion cycles in the graphs of FIGS. 7, 8 and 9, respectively.

time). It is also ascertained from FIG. 8 that the percent drop of output level is in proportion to the square root of the number of abrasion cycles. As to the jitter, it is seen from FIG. 9 that the jitter is linearly correlated to the number of abrasion cycles.

It is seen from the above results that when any of reflectance, output level and jitter is employed as an item for evaluation, its change is represented as a function of abrasion time and substantially reflects the mar resistance of the light-transparent substrate surface. That is, the evaluation method of the invention is an advantageous method for evaluating the mar resistance, abrasion resistance or other factor of a light-transparent substrate in an optical information medium.

What is claimed is:

1. An optical information medium comprising a light-transparent substrate and an information recording layer, wherein optical recording and/or reading is performed with a laser beam that enters said information recording layer from the light-transparent substrate side, wherein said medium includes a cured polysilazane film disposed on the laser beam incident side of said light-transparent substrate, and said light-transparent substrate or said light-transparent substrate having the cured polysilazane film integrated thereon has a tensile modulus of at least 200 MPa.

2. The optical information medium of claim 1 wherein said light-transparent substrate includes a resin layer of 30 to 300 $\mu$m thick.

3. The optical information medium of claim 1 wherein said cured polysilazane film has a thickness of 0.2 to 50 $\mu$m.

4. The optical information medium of claim 1 wherein the laser beam incident side surface has a pencil hardness of at least HB.

5. The optical information medium of claim 1 wherein said cured polysilazane film is a laminate including a plurality of films of different compositions, in which a cured

TABLE 3

| Abrasion cycles | | 0 | 5 | 10 | 20 | 40 | 80 | 100 | 500 |
|---|---|---|---|---|---|---|---|---|---|
| Sample No. 1 | Reflectance, % | 22.5 | — | — | — | — | — | 21.3 | 19.4 |
| | Drop, % | — | — | — | — | — | — | 5.5 | 14.0 |
| | Output (relative value) | 100 | — | — | — | — | — | 94.0 | 82.5 |
| | Drop, % | — | — | — | — | — | — | 6.0 | 17.5 |
| | Jitter, % | 8.5 | — | — | — | — | — | 9.0 | 10.6 |
| Sample No. 2 | Reflectance, % | 22.5 | 22.1 | 21.1 | 21.0 | 19.6 | 18.7 | — | — |
| | Drop, % | — | 2.0 | 6.1 | 6.6 | 12.7 | 16.9 | — | — |
| | Output (relative value) | 100.0 | 95.5 | 91.5 | 90.7 | 86.3 | 78.6 | — | — |
| | Drop, % | — | 4.5 | 8.5 | 9.3 | 13.7 | 21.4 | — | — |
| | Jitter, % | 8.5 | 8.9 | 9.2 | 9.4 | 10.3 | 11.8 | — | — |
| Sample No. 3 | Reflectance, % | 22.5 | 16.0 | Unmeasurable | — | — | — | — | — |
| | Drop, % | — | 28.7 | Unmeasurable | — | — | — | — | — |
| | Output (relative value) | 100 | 61.0 | Unmeasurable | — | — | — | — | — |
| | Drop, % | — | 39.0 | Unmeasurable | — | — | — | — | — |
| | Jitter, % | 8.5 | 16 | Unmeasurable | — | — | — | — | — |

As is evident from Table 3 and FIGS. 7 to 9, excellent mar resistance is provided by constructing the laser beam incident side surface of an optical disk from a cured polysilazane film.

It is ascertained from FIG. 7 that when the abrasive wheel test specified in ISO 9352 was used as the abrasion procedure in the evaluation method of the invention, the percent drop of reflectance in all the media is in proportion to the square root of the number of abrasion cycles (i.e., abrasion film of inorganic polysilazane and a cured film of organic group-introduced polysilazane are stacked in the described order when said cured polysilazane film is viewed from the laser beam incident side.

6. The optical information medium of claim 1 further comprising a functional layer on the laser beam incident side of said cured polysilazane film, said functional layer having at least one function selected from among lubricity, water repellency and oil repellency.

7. The optical information medium of claim 6 wherein said functional layer has a thickness of up to 500 nm.

8. The optical information medium of claim 6 wherein said functional layer is made of a compound having hydrolyzable silyl groups.

9. In connection with an optical information medium comprising a light-transparent substrate and an information recording layer, wherein optical recording and/or reading is performed with a laser beam that enters said information recording layer from the light-transparent substrate side, a method for evaluating the optical information medium for mar resistance on its laser beam incident side surface, comprising the steps of
intentionally abrading the laser beam incident side surface of the optical information medium,
then measuring a recording/reading characteristic, and evaluating the mar resistance of the laser beam incident side surface on a basis of the measured value.

10. The method of claim 9 wherein an abrasive wheel as prescribed by ISO 9352 is used as the means for intentionally abrading the laser beam incident side surface of the optical information medium.

11. The method of claim 9 wherein #0000 steel wool is used as the means for intentionally abrading the laser beam incident side surface of the optical information medium.

* * * * *

UNITED STATES PATENT AND TRADEMARK OFFICE
CERTIFICATE OF CORRECTION

PATENT NO. : 6,576,320 B2
DATED : June 10, 2003
INVENTOR(S) : Hayashida et al.

It is certified that error appears in the above-identified patent and that said Letters Patent is hereby corrected as shown below:

<u>Title page,</u>
Item [75], should read:
-- [75]   Inventors: Naoki Hayashida, Tokyo (JP);
                    Hideki Hirata, Tokyo (JP);
                    Toshifumi Tanaka, Tokyo (JP) --

Signed and Sealed this

Eighteenth Day of November, 2003

JAMES E. ROGAN
*Director of the United States Patent and Trademark Office*